(12) United States Patent
Mertens et al.

(10) Patent No.: US 7,528,201 B2
(45) Date of Patent: May 5, 2009

(54) SYNTHESIS OF SILICOALUMINOPHOSPHATE MOLECULAR SIEVES

(75) Inventors: Machteld M. Mertens, Boortmeerbeek (BE); An Verberckmoes, Serskamp (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 817 days.

(21) Appl. No.: 11/048,072

(22) Filed: Jan. 31, 2005

(65) Prior Publication Data

US 2006/0135349 A1 Jun. 22, 2006

Related U.S. Application Data

(60) Provisional application No. 60/638,712, filed on Dec. 22, 2004.

(51) Int. Cl.
*C08F 2/00* (2006.01)
*C07C 1/20* (2006.01)
*B01J 27/182* (2006.01)

(52) U.S. Cl. .................. 526/75; 585/327; 585/329; 585/639; 502/214

(58) Field of Classification Search ................ 585/327, 585/329, 640; 526/75; 502/214
See application file for complete search history.

(56) References Cited

U.S. PATENT DOCUMENTS

| | | | |
|---|---|---|---|
| 3,492,090 A | 1/1970 | Jenkins | 23/113 |
| 3,886,094 A | 5/1975 | Pilato et al. | 252/451 |
| 4,267,158 A | 5/1981 | Christophliemk et al. | 423/329 |
| 4,278,649 A | 7/1981 | Christophliemk et al. | 423/329 |
| 4,371,510 A | 2/1983 | Christophliemk et al. | 423/329 |
| 4,440,871 A | 4/1984 | Lok et al. | 502/214 |
| 4,591,491 A | 5/1986 | Christophliemk et al. | 423/329 |
| 4,661,334 A | 4/1987 | Latourrette et al. | 423/329 |
| 4,818,509 A | 4/1989 | Dwyer et al. | 423/329 |
| 4,859,442 A | 8/1989 | Zones et al. | 423/277 |
| 4,946,545 A | 8/1990 | Engel et al. | 156/623 R |
| 5,098,673 A | 3/1992 | Engel et al. | 422/245 |
| 5,110,573 A | 5/1992 | Johnson | 423/328 |
| 5,126,308 A | 6/1992 | Barger et al. | 502/214 |
| 5,616,310 A | 4/1997 | Edwards et al. | 423/700 |
| 5,714,133 A | 2/1998 | Schmitt | 423/710 |
| 5,741,751 A | 4/1998 | Miller | 502/208 |
| 5,904,914 A | 5/1999 | Araya | 423/700 |
| 5,989,518 A | 11/1999 | Tannous et al. | 423/717 |
| 6,334,994 B1 | 1/2002 | Wendelbo et al. | 423/718 |
| 6,953,767 B2 * | 10/2005 | Janssen et al. | 502/214 |
| 7,238,846 B2 * | 7/2007 | Janssen et al. | 585/640 |
| 7,247,287 B2 * | 7/2007 | Cao et al. | 423/306 |
| 2001/0054549 A1 | 12/2001 | Park et al. | 204/157.43 |
| 2002/0076376 A1 | 6/2002 | Huo | 423/702 |
| 2003/0003035 A1 | 1/2003 | Stamires et al. | 422/225 |
| 2004/0215044 A1 | 10/2004 | Mertens et al. | 585/639 |

FOREIGN PATENT DOCUMENTS

| | | |
|---|---|---|
| CA | 921895 | 11/1973 |
| CN | 1272402 | 11/2000 |
| DE | 132069 | 8/1978 |
| DE | 138304 | 10/1979 |
| JP | 57111226 | 7/1982 |
| JP | 57129819 | 8/1982 |
| JP | 57166311 | 10/1982 |
| JP | 58213627 | 12/1983 |
| JP | 62256720 | 11/1987 |
| JP | 2002/037622 | 2/2002 |
| JP | 2002068731 | 3/2002 |
| WO | WO 02/070407 | 12/2002 |
| WO | WO 03/011761 | 2/2003 |
| WO | WO 03/048042 | 12/2003 |
| WO | WO 03/048043 | 12/2003 |
| WO | WO 03/048084 | 12/2003 |

OTHER PUBLICATIONS

Aguayo et al, "Role of Acidity and Microporous Structure in Alternative Catalysts for the Transformation of Methanol into Olefins," Applied Catalysis A: General 283 (2005) pp. 197-207.

De Chen et al, "The Effect of Crystal Size of SAPO-34 on the Selectivity and Deactivation of the MTO Reaction", Microporous and Mesoporous Materials, 29, pp. 191-203, (1999).

Braun et al, "Synthesis of AlPO$_4$-5 in Microwave-Heated, Continuous-Flow, High-Pressure Tube Reactor", Microporous and Mesoporous Materials (1998), 23 (1-2), pp. 79-81.

Abstract—Chemical Engineering Communications (1980), 4 (1), pp. 127-133.

API-Derwent Merged File (WPAM) Abstract—Gabelica Z. et al, "Novel Approach to the Synthesis of Molecular Sieves, [including ZSM-5 and NaY Zeolites and Alumino- and Silicoaluminophosphates]: Recrystallization of the Intermediates Isolated from the Gel Phase", ACS 202nd National Meeting/4th Chemical North America Congress (New York Aug. 25-30, 1991) ACS Division of Petroleum Chemistry Preprints V36 N.2 367 (Jul. 1991).

API-Derwent Merged File (WPAM) Abstract—Lopez C., "The Successive Crystallization and Characterization of SAPO-31 and SAPO-11 from the Same Synthesis Gel: Influence on the Selectivity for 1-Butene Isomerization", Zeolites V19 N.2-3, pp. 133-141 (Aug.-Sep. 1997).

HCA Copyright 2002 ACS Abstract—Fujdala, Kyle L. et al, "An Efficient, Single-Source Molecular Precursor to Silicoaluminophosphates", Journal of the American Chemical Society (2001), 123 (41), PP. 10133-10134.

HCA Copyright 2002 ACS Abstract—Batista, Jurka et al, "On the Formation of AlP04-based Molecular Sieves in the Presence of Cyclohexylamine", Aust. J. Chem. (1993), 46 (2), pp. 171-183.

(Continued)

*Primary Examiner*—Fred M Teskin
(74) *Attorney, Agent, or Firm*—Frank E. Reid; David M. Weisberg

(57) ABSTRACT

In a method of synthesizing a silicoaluminophosphate molecular sieve comprising a CHA framework type material, an AEI framework type material, or a material comprising at least one intergrown phase of an AEI framework type and a CHA framework type, the amount of alkali metal present in said synthesis mixture is controlled so as to reduce the crystal size of the molecular sieve and/or to increase the AEI character of the intergrown phase.

26 Claims, 2 Drawing Sheets

OTHER PUBLICATIONS

HCA Copyright 2002 ACS Abstract—Vistad, B. et al, "Identification of a Key Precursor Phase for Synthesis of SAPO-34 and Kinetics of Formation Investigated by in Situ X-ray Diffraction", American Chemical Society, Journal of Physical Chemistry B (2001), 105 (50), pp. 12437-12447.

HCA Copyright 2002 ACS Abstract—Venkatathri, N. et al, "Isolation and Characterization of a Novel Lamellar-Type Aluminophosphate, AlPO4-L, a Common Precursor for AlPO4 Molecular Sieves", Elsevier Science B.V., Microporous and Mesoporous Materials (1998), 23 (5-6), pp. 277-285.

HCA Copyright 2002 ACS Abstract—Sun, Jiayao et al, "Phase Transitions of Hereto Atom-Substituted Molecular Sieves Me-VPI-5 (Me=Mg, Ti, Sn, Si) and their Influence on Spectra Structures of Eu(III) Ion", Gaodeng Xuexiao Huaxue Xuebao (1996), 17 (3), pp. 345-349.

HCA Copyright 2002 ACS Abstract—Ito, T. et al, "Xenon-129 NMR Study of the Crystallization of SAPO-37", Stud. Surf. Sci. Catal. (1991), 60 (Chem. Microporous Cryst.), pp. 11-20.

Caplus Copyright 2002 ACS Abstract—Tiemann, Michael et al, "Mesoporous Aluminophosphates from a Single-Source Precursor", Royal Society of Chemistry, Chemical Communications (Cambridge, United Kingdom) (2002), (5), pp. 406-407.

Caplus Copyright 2002 ACS Abstract—Tao, Mingtao et al, "Synthesis of BAPO-5", Fushun Shiyou Xueyuan Xuebao (2000), 20 (4), pp. 7-11.

Caplus Copyright 2002 ACS Abstract—Kirchner, R.M. et al, "The Structures of As-Synthesized AlPO4-53 (A), Calcined Dehydrated AlPO4-53 (B), and AlPO4-53 (C), a New Phase Determined by the FOCUS Method", Elsevier Science B.V., Microporous and Mesoporous Materials (2000), 39 (1-2), pp. 319-332.

Caplus Copyright 2002 ACS Abstract—Canesson, L. et al, "Synthesis and Characterization of Cobalt-Containing Hydrated Aluminophosphate Molecular Sieves CoAPO4-H3", Elsevier Science B.V., Microporous and Mesoporous Materials (1998), 26 (1-3), pp. 117-131.

Caplus Copyright 2002 ACS Abstract—Vidal, L. et al, "A Novel Monoclinic AlPO4-Sodalite Formed in the Presence of Dimethylformamide as Template and Solvent", Elsevier Science B.V., Microporous and Mesoporous Materials (1998), 24 (4-6), pp. 189-197.

Caplus Copyright 2002 ACS Abstract—Rajic, Nevenka et al, "A Novel Triclinically Deformed Chabazite-Like Aluminophosphate Prepared in the Presence of Tris (1, 2-Diaminoethane) Nickel (II) Chloride", Elsevier Science B.V., Microporous and Mesoporous Materials (1998), 24 (1-3), pp. 83-87.

Caplus Copyright 2002 ACS Abstract—Eshchenko, L.S. et al, "Investigation of Crystallization Conditions of Porpous Aluminophosphates", Belaruskaya Navuka, Vestsi Akademii Navuk Belarusi, Seryya Khimichnykh Navuk (1996), (4), pp. 5-9.

Caplus Copyright 2002 ACS Abstract—Feng, Pingyun et al, "Synthesis and Characterization of Mesostructured Aluminophosphates using the Fluoride Route", Royal Society of Chemistry, Chemical Communications (Cambridge) (1977), (10), pp. 949-950.

Caplus Copyright 2002 ACS Abstract—Clark, Howard W. et al, "Synthesis and Characterization of AlPO-41 in a Mixed Solvent System", Microporous Mater. (1996), 6 (3), pp. 115-124.

Caplus Copyright 2002 ACS Abstract—Cheng, Chi-Feng et al, "Synthesis and Characterization of CAM-1, a Novel Aluminophosphate Molecular Sieve Precurssor", J. Chem. Soc., Farady Trans. (1995), 91 (21), pp. 3995-3999.

Caplus Copyright 2002 ACS Abstract—Kabanets, L. Ph. et al, "Effect of the Synthesis Conditions and the Nature of the Template on the Structure of Crystalline Microporous Aluminophosphates", Ukr. Khim. Zh. (Russ. Ed.) (1994), 60 (9-10), pp. 595-599.

Caplus Copyright 2002 ACS Abstract—Huo, Qisheng, et al, "Synthesis, Characterization and Phase Transition of the 20-Membered Ring AlPO4: JDF-20", Conference, Proc. Int. Zeolite Conf., 9th (1993), Meeting Date 1992, vol. 1, pp. 279-286; Editor(s) Von Ballmoos, Ronald; Higgins, John B.; Treacy, Michael .J.—Publisher: Butterworth-Heinemann, Boston Mass.

Caplus Copyright 2002 ACS Abstract—Oliver, Scott et al, "New Insights Into the Mode of Formation of AlP04-n Molecular Sieves", Stud. Surf. Sci. Catal. (1994), 84 (Zeolites and Related Microporous Materials, Pt. A), pp. 219-225.

Caplus Copyright 2002 ACS Abstract—Schott-Darie, C. et al, "Further Results in the Synthesis of Microporous Alumino- and Gallophosphates in the Presence of Fluoride", Stud. Surf. Sci. Catal. (1994), 83 (Zeolites and Microporous Crystals), pp. 3-10.

Caplus Copyright 2002 ACS Abstract—Akolekar, D.B. et al, "MAPO-43 Molecular Sieve: Synthesis, Characterization and Thermal Stability", Microporous Mater. (1994), 2 (2), pp. 137-144.

Caplus Copyright 2002 ACS Abstract—Ohnishi, Naoyuki, et al, "Hexagonal-Orthorhombic Phase Transformation of AlPO4-5 Aluminophosphate Molecular Sieve", Microporous Mater. (1993), 2 (1), pp. 73-74.

Caplus Copyright 2002 ACS Abstract—Tian, Wentong et al, "Synthesis of DBA-VPI-5 and its Phase Transformation", Chin. Chem. Lett. (1991), 2 (12), pp. 979-928.

Caplus Copyright 2002 ACS Abstract—Duncan, B. et al, "Template-Free Synthesis of the Aluminophosphates H1 through H4", Bull. Soc. Chim. Fr. (1992), 129 (1), pp. 98-110.

Caplus Copyright 2002 ACS Abstract—O'Hare, Dermot et al, "Time-Resolved, in Situ X-Ray Diffraction Studies of the Hydrothermal Syntheses of Microporous Materials", Elsevier Science B.V., Microporous and Mesoporous Materials (1998), 21 (4-6), pp. 253-262.

HCA Copyright 2002 ACS Abstract—Christensen, A. Noerlund et al, "In-Situ Investigation of Magnesium Aluminophosphate Synthesis by Synchrotron X-Ray Powder Diffraction", Munksgaard, Acta Chemica Scandinavica (1997), 51 (3), pp. 249-258.

HCA Copyright 2002 ACS Abstract—Vidal, L. et al, "Crystallization Mechanisms of Novel Aluminophosphate Materials in Quasi Non Aqueous Mono- and Dialkylformamide Media", Conference, Proceedings of the International Zeolite Conference, 12th, Baltimore, Jul. 5-10, 1998 (1999), Meeting Date 1998, vol. 3, pp. 1633-1639, Editor(s): Traecy, M.M.J.; Publisher: Materials Research Society, Warrendale, PA.

Caplus Copyright 2002 ACS Abstract—Batista, Jurka et al, "On the Formation of the Cobalt Silicoaluminophosphate CoAPSO44", Zeolites (1992), 12 (8), pp. 925-928.

ALIT Copyright 2002 API Abstract—Xu R. et al, "Synthesis and Characterization of a New Microporous Aluminophosphate Al (sub) 2P (sub) 20 (sub) 8 OCH (sub) 2CH (sub) 2NH (sub 3 with an Open-Framework Analogous to AlPO (sub) 4-D", Microporous and Mesoporous Materials 39/1-2, pp. 281-289 (Sep. 2000).

Caplus Copyright 2002 ACS Abstract—Kunii, Katsuyuki et al, "Template-Free Synthesis and Absorption Properties of Microporous Crystal AlPO4-H3", Elsevier Science B.V., Microporous and Mesoporous Materials (2001), 50 (2-3), pp. 181-185.

Caplus Copyright 2002 ACS Abstract—Prakash, A.M. et al, "A Novel Aluminophosphate Precursor that Transforms to AlPO4-5 Molecular Sieve at High Temperature", Royal Society of Chemistry, Chemical Communications (Cambridge) (1997), (22), pp. 2221-2222.

HCA Copyright 2002 ACS Abstract—Buhl, J.C. et al, "The Transformation of Zeolite A and X into Nitrate Cancrinite Under Low Temperature Hydrothermal Reaction Conditions", Elsevier Science B.V., Studies in Surface Science and Catalysis (2001), 135 (Zeolites and Mesoporous Materials at the Dawn of the 21t Century), pp. 184-191.

HCA Copyright 2002 ACS Abstract—Oh, Hyung-Seuk et al, "Synthesis of MFI-Type Zeolites under Atmospheric Pressure", Korean Institute of Chemical Engineers, Korean Journal of Chemical Engineering (2001), 18 (1), pp. 113-119.

HCA Copyright 2002 ACS Abstract—Landry, Christopher C. et al, "Phase Transformations in Mesostructured Silica/Surfactant Composites. Mechanisms for Change and Applications to Materials Synthesis", American Chemical Society, Chemistry of Materials (2001), 13 (5), pp. 1600-1608.

HCA Copyright 2002 ACS Abstract—Caputo, D. et al, "A Preliminary Investigation on Kinetics of Zeolite A Crystallization Using Optical Diagnosis", Elsevier-Science S.A., Materials Chemistry and Physics (2000), 66 (2-3), pp. 120-125.

HCA Copyright 2002 ACS Abstract—Buhl, Josef-Christian et al, "The Crystallization Kinetics of Nitrate Cancrinite Na7.6 [AlSiO4] 6 (NO3) 1.6 (H20) 2 Under Low Temperature Hydrothermal Conditions", Akademiai Kiado, Reaction Kinetics and Catalysis Letters (2000), 69 (1), pp. 15-21.

HCA Copyright 2002 ACS Abstract—Awate, S.V., et al, "Monitoring the Hydrothermal Crystallization of Ga/ZSM-5 using Sorption and other Conventional Techniques", Multi-Science Publishing Co. Ltd., Adsorption Science & Technology (1999), 17 (8), pp. 651-665.

HCA Copyright 2002 ACS Abstract—Walton, Richard I. et al, "An in Situ Energy-Dispersive X-ray Diffraction Study of the Hydrothermal Crystallizations of Open-Framework Gallium Oxyfluorophosphates with the ULM-3 and ULM-4 Structures", American Chemical Society, Chemistry of Materials (1999), 11 (11), pp. 3201-3209.

HCA Copyright 2002 ACS Abstract—Hartmann, Martin et al, "Mechnical Stability of Mesoporous Molecular Sieve MCM-48 Studied by Absorption of Benzene, n-Heptane, and Cyclohexane", American Chemical Society, Journal of Physical Chemistry B (1999), 103 (30), pp. 6230-6235.

HCA Copyright 2002 ACS Abstract—Buhl, J. -Chr et al, "The Crystallization Kinetics of Sodalites Grown by the Hydrothermal Transformation of Kaolinite Studied by 29Si MAS NMR", Elsevier Science B.V., Solid State Nuclear Magnetic Resonance (1997), 9 (2-4), pp. 121-128.

HCA Copyright 2002 ACS Abstract—Rajic, Nevenka et al, "A Novel Open Framework Zincophosphate: Synthesis and Characterization", Zeolites (1995), 15 (8), pp. 672-678.

HCA Copyright 2002 ACS Abstract—Di Renzo Francesco et al, "Precursor Phases and Nucleation of Zeolite TON", Conference, Synth. Microporous Mater. (1992), vol. 1, pp. 115-128.

HCA Copyright 2002 ACS Abstract—Jolchiov, Ja. M. et al, "Thermal X-Ray Study of Channanab Mordenite (Nach, ASSR) and its Caution-Modified Forms", Dokl. Akad. Nauk Az. SSR (1990), 46 (3), pp. 45-52.

HCA Copyright 2002 ACS Abstract—De las Pozas-Del Rio, Carlos et al, "Moessbauer Study of Hydrothermal Transformation of Natural Clinoptilolite into Y and P1 Zeolites", J. Solid State Chem. (1991), 94 (2), 215-219.

HCA Copyright 2002 ACS Abstract—De las Pozas, Carlos et al, "Hydrothermal Transformation of Natural Clinoptilolite to Zeolites Y and P1: Influence of the Sodium, Potassium Content", Zeolites (1989), 9 (1), pp. 33-39.

HCA Copyright 2002 ACS Abstract—Zones, S.I. et al, "Further Studies on the Conversion of Cubic P Zeolite to High Silica Organozeolites", Zeolites (1988), 8 (5), pp. 409-415.

HCA Copyright 2002 ACS Abstract—Dewaele, Nicole et al, "Synthesis and Characterization of ZSM-39 Type Zeolites", Aca Chim. Hung. (1987), 124 (1), pp. 93-108.

HCA Copyright 2002 ACS Abstract—Perez-Pariente, Joaquin et al, "Crystallization Mechanism of Zeolite .beta. from bis (Tetraethylammonium) Oxide, Sodium Oxide, and Potassium Oxide Containing Aluminosilicate Gels", Appl. Catal. (1987), 31 (1), pp. 35-64.

HCA Copyright 2002 ACS Abstract—Bodart, P. et al, "Factors Governing the Synthesis of Zeolites from Silicoaluminate Hydrogels: a Comparative Study of the Crystallization Mechanisms of Zeolites Y, Mordenite, and ZSM-5", J. Chim. Phys. Phys.-Chim. Biol. (1986), 83 (11-12), pp. 777-790.

HCA Copyright 2002 ACS Abstract—Van Santen, R.A. et al, "The Role of Interfacial Energy in Zeolite Synthesis", Stud. Surf. Sci. Catal. (1986), 28 (New Dev. Zeolite Sci. Technol.), pp. 169-175.

HCA Copyright 2002 ACS Abstract—Lutz, Wolfgang et al, "Formation of a Special Intermediate During Phase Transformation of Zeolite NaA to Nepheline", Cryst. Res. Technol. (1986), 21 (10), pp. 1339-1344.

HCA Copyright 2002 ACS Abstract—Dewaele, Nicole et al, "Synthesis and Characterization of Faujasite-Type Zeolites, I. Multinuclear NMR Characterization of Liquid and Solid Intermediate Phases formed during Synthesis of Zeolite Y", Acta Chim. Hung. (1985), 119 (2-3), pp. 233-244.

HCA Copyright 2002 ACS Abstract—Gabelica, Z. et al, "On the Use of Multinuclear High Resolution Solid State NMR Spectroscopy to Characterize Intermediate Phases formed during ZSM-5 Zeolite Synthesis", Conference, Proc. Int. Zeolite Conf., 6th (1984), Meeting Date 1983, pp. 914-924. Editor(s): Olson, David; Bisio, Attilio, Publisher: Butterworth, Guildford, UK.

HCA Copyright 2002 ACS Abstract—Sexton, B.A. et al, "Characterization of Copper-Exchanged Na-A, X and Y Zeolites with X-Ray Photoelectron Spectroscopy and Transmission Electron Microscopy", J. Electron Spectrosc. Relat. Phenom. (1985), 35 (1-2), pp. 27-43.

HCA Copyright 2002 ACS Abstract—Gabelica, Z. et al, "Incorporation of Boron in Tetrahedral Sites of ZSM-5 Framework During Crystallization: a High Resolution Solid State MAS boron-11 NMR Study", Stud. Surf. Sci. Catal. (1984), 19 (Catal. Energy Scene), pp. 113-121.

HCA Copyright 2002 ACS Abstract—Nastro, A. et al, "Competitive Roles of Alkali and TPA Cations During Nucleation and Growth of ZSM-5 Zeolite", Stud. Surf. Sci. Catal. (1984), 19 (Catal. Energy Scene), pp. 131-137.

HCA Copyright 2002 ACS Abstract—Nastro, Alfonso et al, "Zeolite Synthesis in Systems Containing Organic Cations. II. ZSM-5 Crystallization from Sodium, Potassium-Ammonium-TPA Systems", Ann. Chim. (Rome) (1984), 74 (7-8), pp. 579-587.

HCA Copyright 2002 ACS Abstract—Bodart, Philippe et al, "Multinuclear Solid-State NMR Study of Mordenite Crystallization", Nato Asi Ser., Ser. E (1984), 80 (Zeolites: Sci. Technol.), pp. 211-226.

HCA Copyright 2002 ACS Abstract—Borade, R.B. et al, "Kinetics of Crystallization of ZSM-5 Zeolites", Indian J. Technol. (1983), 21 (9), pp. 358-362.

HCA Copyright 2002 ACS Abstract—Dibble, W.E., Jr. et al, "Kinetic Model of Zeolite Paragenesis in Tuffaceous Sediments", Clays Clay Miner. (1981), 29 (5), pp. 323-330.

HCA Copyright 2002 ACS Abstract—Ratterman, Nancy G. et al, "Zeolite Mineral Reactions in a Tuff in the Laney Member of the Green River Formation, Wyoming", Clays Clay Miner. (1981), 29 (5), pp. 365-377.

HCA Copyright 2002 ACS Abstract—Selvam, T. et al, "Hydrothermal Ransformation of a Layered Silicate, Na-Magadiite, Into Mordenite Zeolite", Elsevier Science B.V., Studies in Surface Science and Catalysis (2001), 135 (Zeolites and Mesoporous Materials at the Dawn of the 21st Century), pp. 411-419.

Caplus Copyright 2002 ACS Abstract—Pal-Borbely, G. et al, "Solid-State Recrystallization of Aluminum-Containing Kanemite Varieties to Ferrierite", Elsevier Science B.V., Microporous and Mesoporous Materials (2000), 35-36, pp. 573-584.

Caplus Copyright 2002 ACS Abstract—Pal-Borbely, Gabriella et al, "Synthesis and Characterization of a Ferrierite made by Recrystallization of an Aluminum-Containing Hydrated Magadiite", Elsevier Science B.V., Microporous and Mesoporous Materials (1998), 22 (1-3), pp. 57-68.

Caplus Copyright 2002 ACS Abstract—Pal-Borbely, Gabriella et al, "Recyrstallization of Magadiite Varieties Isomorphically Substituted with Aluminum to MFI and MEL Zeolites", Elsevier, Microporous Materials (1997), 11 (1-2), pp. 45-51.

ALIT—(C) API Abstract—Hartmann M. et al, "Mechanical Stability of the Mesoporous Molecular Sieve MCM-48 Studied by Absorption of Benzene, N-Heptane, and Cyclohexane", Journal of Physical Chemistry B V103 N.30, pp. 6230-6235 (Jul. 29, 1999).

ALIT—(C) API Abstract—Joshi P.N. et al, "Physicochemical Characterization of the Intermediate Phases Obtained during the Hydrothermal Crystallization of LTL [(Linde type L)] Zeolites", Journal of Physical Chemistry V99 N. 12, pp. 4225-4229 (Mar. 23, 1995).

ALIT—(C) API Abstract—Nagy J.B. et al, "Characterization of Crystalline and Amorphous Phases during the Synthesis of (TPA, M)—ZSM-5 Zeolites (M=Li, Na, K)", J. Chem. Soc., Faraday Trans. I V85 N.9, pp. 2749-2769 (Sep. 1989).

ALIT—(C) API Abstract—Perez-Pariente J. et al, "Crystallization Mechanism of Zeolite Beta From (TEA)20 ((Tetraethylammonium Oxide)), NA20, and K20 Containing Aluminosilicate Gels", Appl. Catal. (ISSN 016609834) V31 N.1, pp. 35-64 (May 15, 1987).

Caplus Copyright 2002 ACS Abstract—Zones, S.I., "Conversion of Faujasites to High-Silica Chabazite SSZ-13 in the Presence of N, N, N-Trimethyl-1-Adamantammonium Iodide", J. Chem. Soc., Faraday Trans. (1991), 87 (22), pp. 3709-3716.

Caplus Copyright 2002 ACS Abstract—Zones, Stacey I., "Direct Hydrothermal Conversion of Cubic P Zeolite to Organozeolite SSZ-13", J. Chem. Soc., Faraday Trans. (1990), 86 (20), pp. 3467-3472.

Caplus Copyright 2002 ACS Abstract—Zones, S.I. et al, "Novel Zeolite Transformations: the Template-Mediated Conversion of Cubic P Zeolite to SSZ-13", Zeolites (1988), 8 (3), pp. 166-174.

Caplus Copyright 2002 ACS Abstract—Zones, S.I. et al, "Use of Modified Zeolites as Reagents Influencing Nucleation in Zeolite Synthesis", Stud. Surf. Sci. Catal. (1995), 97 (Zeolites: A Refined Tool for Designing Catalytic Sites), pp. 45-52.

ALIT Copyright 2002 API Abstract—Gabelica Z et al, "Novel Approach to the Synthesis of Molecular Sieves, [including ZSM-5 and NaY Zeolites and Alumino- and Silicoaluminophosphates]: Recrystallization of the Intermediates Isolated from the Gel Phase", ACS 2002nd National Meeting/4th Chemical North America Congress (New York Aug. 25-30, 1991) ACS Division of Petroleum Chemistry Preprints V36 N.2 367 (Jul. 1991).

* cited by examiner

SYNTHESIS OF SILICOALUMINOPHOSPHATE MOLECULAR SIEVES

CROSS-REFERENCE TO RELATED APPLICATIONS

The present application claims the benefit of U.S. Provisional Application No. 60/638,712, filed Dec. 22, 2004, said application hereby fully incorporated by reference.

FIELD OF INVENTION

This invention relates to the synthesis silicoaluminophosphate molecular sieves and to the use of the resultant molecular sieves as catalysts for the conversion of oxygenates, particularly methanol, to olefins, particularly ethylene and propylene.

BACKGROUND OF INVENTION

Light olefins, such as ethylene, propylene, butylenes and mixtures thereof, serve as feeds for the production of numerous important chemicals and polymers. Typically, $C_2$-$C_4$ light olefins are produced by cracking petroleum refinery streams, such as $C_3$+ paraffinic feeds. In view of limited supply of competitive petroleum feeds, production of low cost light olefins from petroleum feeds is subject to waning supplies. Efforts to develop light olefin production technologies based on alternative feeds have therefore increased.

An important type of alternative feed for the production of light olefins is oxygenates, such as $C_1$-$C_4$ alkanols, especially methanol and ethanol; $C_2$-$C_4$ dialkyl ethers, especially dimethyl ether (DME), methyl ethyl ether and diethyl ether; dimethyl carbonate and methyl formate, and mixtures thereof. Many of these oxygenates may be produced from alternative sources by fermentation, or from synthesis gas derived from natural gas, petroleum liquids, carbonaceous materials, including coal, recycled plastic, municipal waste, or any organic material. Because of the wide variety of sources, alcohol, alcohol derivatives, and other oxygenates have promise as economical, non-petroleum sources for light olefin production.

The preferred process for converting an oxygenate feedstock, such as methanol, into one or more olefin(s), primarily ethylene and/or propylene, involves contacting the feedstock with a crystalline molecular sieve catalyst composition. Among the molecular sieves that have been investigated for use as oxygenate conversion catalysts, small pore silicoaluminophosphates (SAPOs), such as SAPO-34 and SAPO-18, have shown particular promise. SAPO-34 belongs to the family of molecular sieves having the framework type of the zeolitic mineral chabazite (CHA), whereas SAPO-18 belongs to the family of molecular sieves having the AEI framework type. In addition to regular ordered silicoaluminophosphate molecular sieves, disordered structures, such as planar intergrowths containing both AEI and CHA framework type materials, are known and have shown activity as oxygenate conversion catalysts.

It is also known that silicoaluminophosphates of relatively small particle size are particularly effective in the conversion of methanol to olefins. Thus, for example, De Chen, et al., reports that SAPO-34 crystals of 0.4 to 0.5 µm gave the largest capacity of olefin formation (*Microporous and Mesoporous Materials*, 29, 191-203, 1999). In this work, the crystals were obtained from a single batch of crystals, which was fractionated to obtain the differently sized crystals evaluated.

U.S. Pat. No. 5,126,308 discloses that ELAPO molecular sieves, wherein EL is a metal selected from the group consisting of silicon, magnesium, zinc, iron, cobalt, nickel, manganese, chromium and mixtures thereof, composed of particles at least 50% of which have a particle size less than 1.0 µm and no more than 10% of which have a particle size greater than 2.0 µm, exhibit improved selectivity and catalyst life in the catalytic conversion of methanol to olefins.

International Patent Publication No. WO03/048084, published Jun. 12, 2003, discloses that increased selectivity to ethylene and propylene is obtained in the catalytic conversion of methanol to olefins when the catalyst comprises an ELAPO molecular sieve, wherein EL is a metal selected from the group consisting of silicon, magnesium, zinc, iron, cobalt, nickel, manganese, chromium and mixtures thereof, having a platelet-type crystal morphology, wherein the average smallest crystal dimension of the crystals is at least 0.1 micron and the aspect ratio of the crystals is less than or equal to 5.

Thus, in order to synthesize silicoaluminophosphate molecular sieves having CHA and/or AEI framework types that are effective in the catalytic conversion of oxygenates to olefins, it is important to be able to control not only the framework structure of the molecular sieve but also its crystal size and in particular to be able to reliably produce materials having a small average crystal size and a low variation in the size between individual crystallites.

The synthesis of silicoaluminophosphate molecular sieves having CHA and/or AEI framework types involves mixing reactive sources of silicon, phosphorus and aluminum in the presence of water and an organic directing agent, particularly tetraethylammonium hydroxide (TEAOH), then heating the mixture to a crystallization temperature, typically 150° to 250° C., and thereafter maintaining the mixture at the crystallization temperature for up to 150 hours. Although a variety of suitable silicon, phosphorus and aluminum sources are available, most commercial sources contain significant levels of impurities, including metals. For example, certain commercial sources of TEAOH contain as much as 1.6 wt % potassium and 0.05 wt % of sodium, whereas phosphoric acid, a preferred phosphorus source, frequently contains in excess of 0.01 wt % of alkali metal.

Study of the synthesis of silicoaluminophosphate molecular sieves has shown that the level of alkali metal, particularly sodium and potassium, impurities in the synthesis mixture has an important role in determining the average crystal size and the crystal size distribution of CHA and AEI-containing materials. In particular, it has now been found that materials having an average ($d_{50}$) crystal size of less than 2.2 micron and a relatively low crystal size distribution [$(d_{90}-d_{10})/d_{50}$=<1.0] can be obtained with synthesis mixtures containing between about 0.08 and about 0.9 g of alkali metals/mole of alumina. In contrast, when the alkali metal concentration increases above 0.9 g/mole of alumina, the crystal size variation increases whereas, when the alkali metal concentration falls below about 0.08 g/mole of alumina, there is a loss in crystal size reproducibility.

In addition, in the synthesis of AEI/CHA intergrowths, it is found that the level of alkali metal impurities in the synthesis mixture has an important role in determining the composition of the intergrowth. Thus, when the alkali metal concentration in the synthesis mixture is less than 1.0 g/mole of alumina, the production of CHA-rich materials is favored, whereas AEI-rich materials tend to be produced at alkali metal concentrations of at least 1.0 g/mole of alumina.

Synthesis of silicoaluminophosphate molecular sieves, including SAPO-34, is described in U.S. Pat. No. 4,440,871. According to this patent, in synthesizing these SAPO compositions, it is preferred that the reaction mixture be essentially free of alkali metal cations and have a composition expressed in terms of molar oxide ratios is as follows:

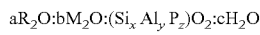

wherein "R" is an organic templating agent, "a" has a value great enough to constitute an effective concentration of "R" and is within the range of >0 to 3; "b" has a value of zero to 2.5; "c" has a value of from zero to 500, preferably 2 to 30; "x", "y" and "z" represent the mole fractions, respectively of silicon, aluminum and phosphorus in the $(Si_xAl_yP_z)O_2$ constituent, and each has a value of at least 0.01. Apart from pH control, no specific reason for the preference for alkali-free reaction mixtures is given in U.S. Pat. No. 4,440,871.

U.S. Pat. No. 5,741,751 discloses a process for preparing silicoaluminophosphate molecular sieves, such as SAPO-11, from a reaction mixture containing an active source of phosphorus and a particulate hydrated alumina having an average particle size of less than about 40 micron, a particle density of less than about 1.0 g/cm$^3$ and an alkali content of less than 0.12 wt %. There is no disclosure of producing CHA and/or AEI framework-type materials.

International Patent Publication No. WO03/048042, published Jun. 12, 2003, discloses a process for the manufacture of a SAPO-34 crystalline molecular sieve by hydrothermal treatment of a surfactant-free synthesis mixture containing a structure-directing agent and sources of silicon, aluminum and phosphorus, wherein the source of silicon is a tetraalkyl orthosilicate. The resultant SAPO-34 crystalline molecular sieve has a mean particle size of at most 400 nm.

International Patent Publication No. WO03/048043, published Jun. 12, 2003, discloses a process for manufacturing a silicoaluminophosphate crystalline molecular sieve, such as SAPO-34, having a mean particle size of at most 400 nm by crystallizing a synthesis mixture comprising sources of aluminum, phosphorus and silicon, wherein the source of silicon is in solution with a water-miscible organic base.

U.S. Pat. No. 7,375,050 discloses a process for producing silicoaluminophosphate molecular sieves, such as CHA framework type materials, in which the average particle size is consistently 1 μm or less and the particle size distribution is such that up to 80% (by number) of the particles are within ±10% of the mean. The process involves crystallization of a synthesis mixture comprising a source of aluminum, a source of phosphorus, at least two organic templates $R^1$ and $R^2$, optionally a source of silicon, and seeds, wherein the molar ratio of organic template $(R+R^2)$ to aluminum (Al) in the synthesis mixture is $\leq 1.25$.

U.S. Pat. No. 6,334,994 discloses a silicoaluminophosphate molecular sieve, referred to as RUW-19, which is said to be an AEI/CHA mixed phase composition. DIFFaX analysis of the X-ray diffraction pattern of RUW-19 as produced in Examples 1, 2 and 3 of U.S. Pat. No. 6,334,994 indicates that these materials are characterized by single intergrown forms of AEI and CHA framework type molecular sieves with AEI/CHA ratios of about 60/40, 65/35 and 70/30. RUW-19 is synthesized by initially mixing an Al-source, particularly Al-isopropoxide, with water and a P-source, particularly phosphoric acid, and thereafter adding a Si-source, particularly colloidal silica and an organic template material, particularly tetraethylammonium hydroxide, to produce a precursor gel. The gel is then put into a steel autoclave and, after an aging period at room temperature, the autoclave is heated to a maximum temperature between 180° C. and 260° C., preferably at least 200° C., for at least 1 hour, with the autoclave being shaken, stirred or rotated during the entire process of aging and crystallization. The resultant RUW-19 crystals are said to have a crystal size between 0.001 and 10 microns.

International Patent Publication No. WO 02/70407, published Sep. 12, 2002, discloses a silicoaluminophosphate molecular sieve, now designated EMM-2, comprising at least one intergrown form of molecular sieves having AEI and CHA framework types, wherein said intergrown form has an AEI/CHA ratio of from about 5/95 to 40/60 as determined by DIFFaX analysis, using the powder X-ray diffraction pattern of a calcined sample of the molecular sieve. Synthesis of the intergrown material is achieved by mixing reactive sources of silicon, phosphorus and a hydrated aluminum oxide in the presence of an organic directing agent, particularly a tetraethylammonium compound. The resultant mixture is stirred and heated to a crystallization temperature, preferably from 150° C. to 185° C., and then maintained at this temperature under stirring for between 2 and 150 hours. The resultant crystals are said to have plate-like morphology with an average smallest dimension of less than 0.1 micron and a ratio of the largest to smallest dimensions of 2 to 20.

SUMMARY OF INVENTION

In one aspect, the invention resides in a method of synthesizing a silicoaluminophosphate molecular sieve comprising a CHA framework type material, an AEI framework type material, or a material comprising at least one intergrown phase of an AEI framework type material and a CHA framework type material, the method comprising:

(a) preparing a synthesis mixture comprising water, an organic directing agent and sources of phosphorus, alumina and silica, wherein the total amount of alkali metal present in said synthesis mixture is from about 0.08 to about 0.90 g/mole of alumina;

(b) heating said synthesis mixture to a crystallization temperature of between about 100° C. and about 300° C.; and Conveniently, the total amount of alkali metal present in said synthesis mixture is from about 0.08 to about 0.80 g/mole of alumina, such as from about 0.10 to about 0.50 g/mole of alumina. Typically, the alkali metal present in said synthesis mixture is sodium and/or potassium.

In one embodiment, said silicoaluminophosphate molecular sieve comprises a CHA framework type material.

In a further embodiment, said silicoaluminophosphate molecular sieve comprises an AEI framework type material.

In yet a further embodiment, said silicoaluminophosphate molecular sieve is a material comprising at least one intergrown phase of an AEI framework type material and a CHA framework type material. Conveniently, said at least one intergrown phase has an AEI/CHA ratio of from about 5/95 to about 40/60, such as about 10/90 to about 30/70, for example about 15/95 to about 20/80, as determined by DIFFaX analysis.

In still yet a further embodiment, said silicoaluminophosphate molecular sieve comprises first and second intergrown forms each of an AEI framework type material and a CHA framework type material. Conveniently, said first intergrown form has an AEI/CHA ratio of from about 5/95 to about 40/60 as determined by DIFFaX analysis and said second intergrown form has a different AEI/CHA ratio from said first intergrown form, such as an AEI/CHA ratio of about 30/70 to about 55/45, such as about 50/50, as determined by DIFFaX analysis.

In a further aspect, the invention resides in a method of synthesizing a silicoaluminophosphate molecular sieve comprising at least one intergrown phase of a CHA framework type material and an AEI framework type material, wherein said at least one intergrown phase has an AEI/CHA ratio of from about 5/95 to about 40/60 as determined by DIFFaX analysis, the method comprising:

(a) preparing a synthesis mixture comprising water, an organic directing agent and sources of phosphorus, alumina and silica, wherein the total amount of alkali metal present in said synthesis mixture is from about 0.08 to about 0.90 g/mole of alumina and said mixture has a molar composition within the following ranges:

$P_2O_5$: $Al_2O_3$ from about 0.6 to about 1.2,
$SiO_2$: $Al_2O_3$ from about 0.12 to about 0.20,
$H_2O$: $Al_2O_3$ from about 25 to about 50, (b) heating said mixture under agitation to a crystallization temperature of between about 100° C. and about 300° C.; and (c) recovering said molecular sieve.

Conveniently, said synthesis mixture (a) has a molar composition within the following ranges:

$P_2O_5$: $Al_2O_3$ from about 0.8 to about 1.1,
$SiO_2$: $Al_2O_3$ from about 0.12 to about 0.15,
$H_2O$: $Al_2O_3$ from about 35 to about 45.

In yet a further aspect, the invention resides in a method of synthesizing a silicoaluminophosphate molecular sieve comprising at least one intergrown phase of a CHA framework type material and an AEI framework type material, wherein said at least one intergrown phase comprises at least 50 wt % of said AEI framework type material as determined by DIFFaX analysis, the method comprising:

(a) preparing a synthesis mixture comprising water, an organic directing agent and sources of phosphorus, alumina and silica, wherein the total amount of alkali metal present in said synthesis mixture is at least 1.00 g/mole of alumina and said mixture has a molar composition within the following ranges:

$P_2O_5$: $Al_2O_3$ from about 0.6 to about 1.2,
$SiO_2$: $Al_2O_3$ from about 0.005 to about 0.15,
$H_2O$: $Al_2O_3$ from about 10 to about 50, (b) heating said mixture under agitation to a crystallization temperature of between about 100° C. and about 300° C.; and (c) recovering said molecular sieve.

In still yet a further aspect, the invention resides in a silicoaluminophosphate molecular sieve synthesized by a method described herein and its use in the conversion of an oxygenate-containing feedstock to a product comprising olefins. Conveniently, said silicoaluminophosphate molecular sieve has an average ($d_{50}$) crystal size of less than 2.2 micron, such as between about 1.5 micron and about 1.9 micron and a ($d_{90}-d_{10}$)/$d_{50}$ crystal size distribution less than 1.0.

DETAILED DESCRIPTION OF THE EMBODIMENTS

Figure 1A:
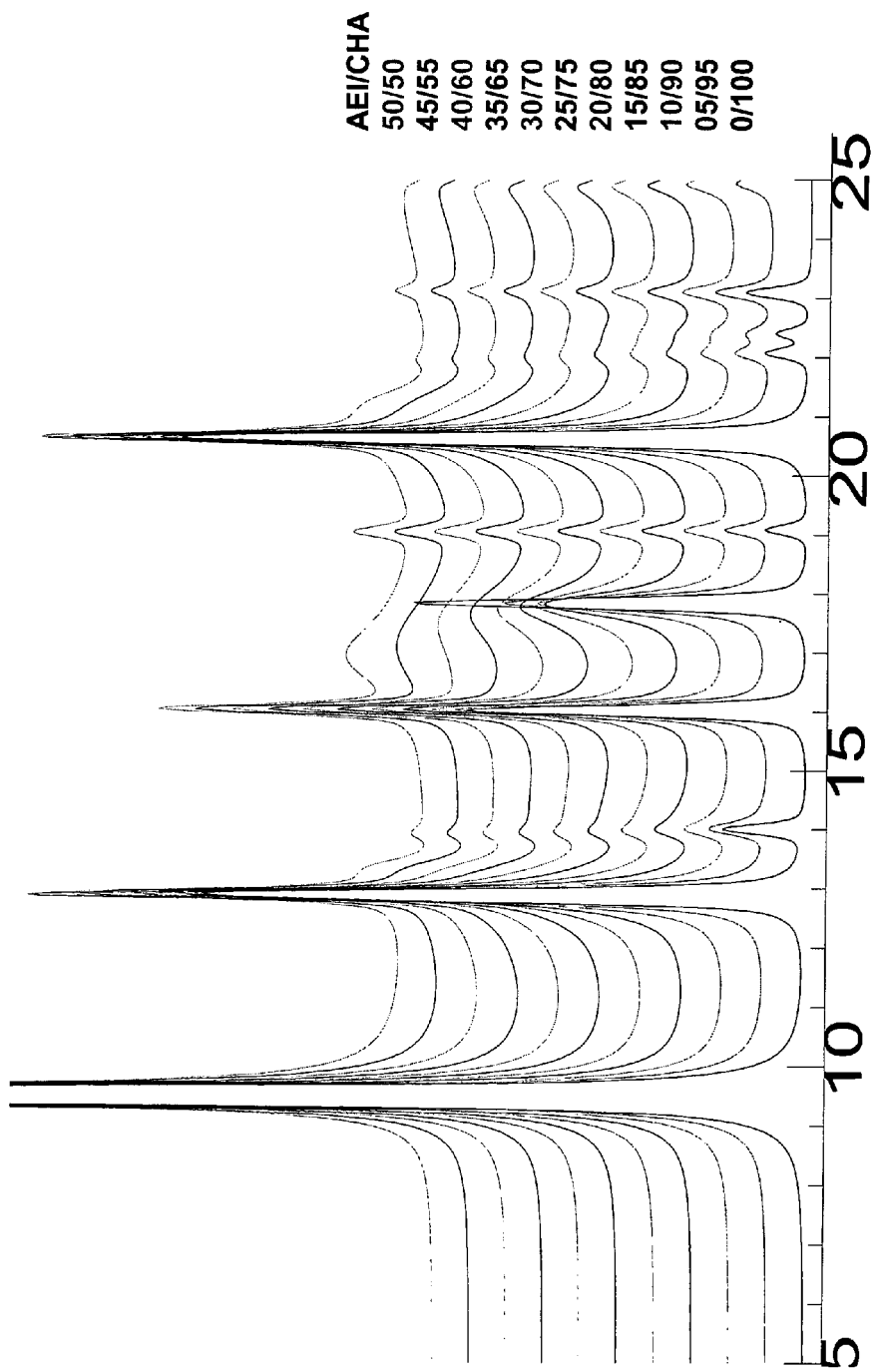
FIGS. 1a and 1b are DIFFaX simulated diffraction patterns for intergrown AEI/CHA phases having varying AEI/CHA ratios.

The present invention is directed to a method of synthesizing silicoaluminophosphate molecular sieves having the AEI and/or CHA framework type and to use of the resultant silicoaluminophosphate molecular sieves in the conversion of an oxygenate-containing feedstock, such as methanol, to a product comprising olefins, such as ethylene and propylene.

Molecular Sieves

Crystalline molecular sieves have a 3-dimensional, four-connected framework structure of corner-sharing [$TO_4$] tetrahedra, where T is any tetrahedrally coordinated cation. In the case of silicoaluminophosphates (SAPOs), the framework structure is composed of [$SiO_4$], [$AlO_4$] and [$PO_4$] corner sharing tetrahedral units.

Molecular sieves have been classified by the Structure Commission of the International Zeolite Association according to the rules of the IUPAC Commission on Zeolite Nomenclature. According to this classification, framework-type zeolite and zeolite-type molecular sieves, for which a structure has been established, are assigned a three letter code and are described in the *Atlas of Zeolite Framework Types,* 5th edition, Elsevier, London, England (2001), which is herein fully incorporated by reference.

One known molecular sieve for which a structure has been established is the material designated as CHA, which is a molecular sieve having pores defined by two sets of generally perpendicular channels each having a cross-sectional dimension about 3.8 Angstrom. CHA framework type materials include the naturally-occurring mineral chabazite, together with a number of synthetic materials including the silicoaluminophosphate molecular sieve, SAPO-34. The preparation and characterization of SAPO-34 have been reported in several publications, including U.S. Pat. No. 4,440,871; J. Chen et al. in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224 (1994); J. Chen et al. in "Catalysis Letters", Vol. 28, pp. 241-248 (1994); A. M. Prakash et al. in "Journal of the Chemical Society, Faraday Transactions" Vol. 90(15), pp. 2291-2296 (1994); Yan Xu et al. in "Journal of the Chemical Society, Faraday Transactions" Vol. 86(2), pp. 425-429 (1990). CHA framework type materials are known to have activity and selectivity in the conversion of oxygenates to lower olefins.

AEI framework type molecular sieves are similar to CHA materials in that their porosity is defined by channels having a cross-sectional dimension about 3.8 Angstrom. Although AEI framework type molecular sieves do not exist in nature, a number of aluminophosphates and silicoaluminophosphates having the AEI framework type have been synthesized, including SAPO-18, ALPO-18 and RUW-18. Moreover, because of their small pore size, AEI-type molecular sieves have been reported as suitable catalysts for a variety of important chemical processes, including the conversion of oxygenates to olefins. See, for example, U.S. Pat. No. 5,095,163, incorporated herein by reference.

Regular silicoaluminophosphate molecular sieves, such as SAPO-18 and SAPO-34, are built from structurally invariant building units, called Periodic Building Units, and are periodically ordered in three dimensions. Structurally disordered structures show periodic ordering in dimensions less than three, i.e. in two, one or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

The intergrown silicoaluminophosphate molecular sieves described herein are disordered planar intergrowths of end-member structures AEI and CHA. For AEI and CHA framework types, the Periodic Building Unit is a double six-ring layer. There are two types of layers "a" and "b", which are topologically identical except "b" is the mirror image of "a". When layers of the same type stack on top of one another, i.e. . . . aaa . . . or . . . bbb . . . , the framework type CHA is generated. When layers "a" and "b" alternate, e.g., . . . abab . . . , a different framework type, namely AEI, is generated. The intergrown molecular sieves described herein comprise stackings of layers "a" and "b" containing regions of CHA framework type and regions of AEI framework type. Each change of CHA to AEI framework type is a stacking disorder or planar fault.

In the case of crystals with planar faults, the interpretation of X-ray diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499-520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp. 543-550.

Figure 1B:
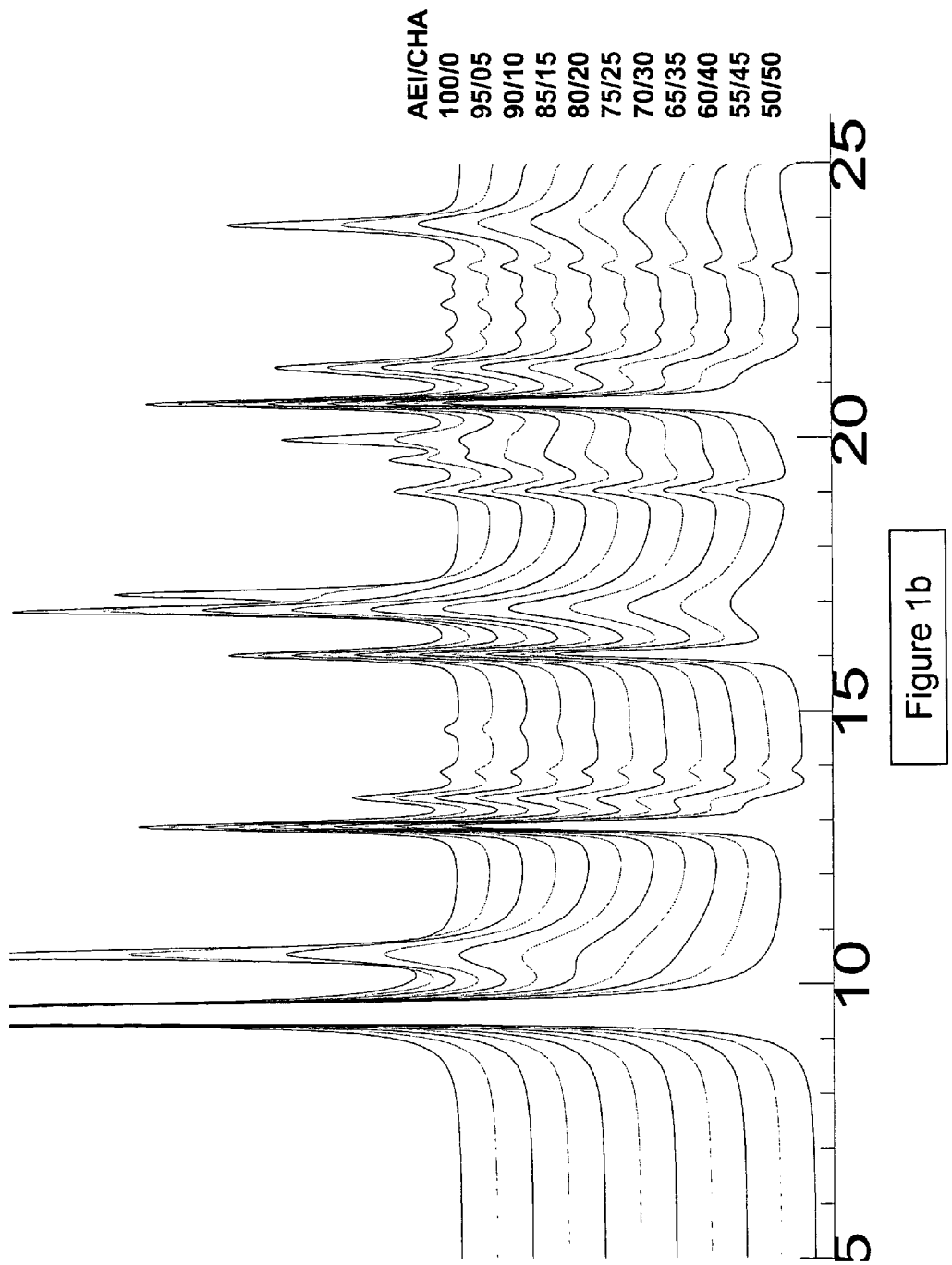

FIGS. 1a and 1b show the simulated diffraction patterns obtained for intergrowths of a CHA framework type molecular sieve with an AEI framework type molecular sieve having various AEI/CHA ratios. FIG. 1a shows the diffraction patterns in the 15 to 35 (2θ) range simulated by DIFFaX for intergrown phases with AEI/CHA ratios of 0/100 (CHA endmember), 10/90 (AEI/CHA=0.11), 20/80 (AEI/CHA=0.25), 30/70 (AEI/CHA=0.41), 40/60 (AEI/CHA=0.67), 50/50 (AEI/CHA=1.00) and 60/40 (AEI/CHA=1.50). FIG. 1b shows the diffraction patterns in the range of 5 to 20 (2θ) simulated by DIFFaX for intergrown phases with AEI/CHA ratios of 0/100 (CHA end-member), 10/90 (AEI/CHA=0.11), 20/80 (AEI/CHA=0.25), 50/50 (AEI/CHA=1.0), 70/30 (AEI/CHA=2.33), 80/20 (AEI/CHA=4.0), 100/0 (AEI end-member). All XRD diffraction patterns are normalized to the highest peak of the entire set of simulated patterns, i.e. the peak at about 9.5 degrees 2θ for pure CHA (AEI/CHA ratio of 0/100). Such normalization of intensity values allows a quantitative determination of mixtures of intergrowths.

As the ratio of AEI increases relative to CHA in the intergrown phase, one can observe a decrease in intensity of certain peaks, for example, the peak at about 2θ=25.0 and an increase in intensity of other peaks, for example the peak at about 2θ=17.05 and the shoulder at 2θ=21.2. Intergrown phases with AEI/CHA ratios of 50/50 and above (AEI/CHA≧1.0) show a broad feature centered at about 16.9 (2θ).

In one embodiment, the intergrown silicoaluminophosphate molecular sieve produced by the method of the invention is at least one intergrowth of an AEI framework type and a CHA framework type, wherein said at least one intergrowth has an AEI/CHA ratio of from about 5/95 to about 40/60, for example from about 10/90 to about 30/70, such as from about 15/85 to about 20/80, as determined by DIFFaX analysis. Such a CHA-rich intergrowth is characterized by a powder XRD diffraction pattern (obtained from a sample after calcination and without rehydration after calcination) having at least the reflections in the 5 to 25 (2θ) range as shown in Table 1 below.

TABLE 1

| 2θ (CuKα) |
|---|
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0 |

The X-ray diffraction data referred to herein are collected with a SCINTAG X2 X-Ray Powder Diffractometer (Scintag Inc., USA), using copper K-alpha radiation. The diffraction data are recorded by step-scanning at 0.02 degrees of two-theta, where theta is the Bragg angle, and a counting time of 1 second for each step. Prior to recording of each experimental X-ray diffraction pattern, the sample must be in the anhydrous state and free of any template used in its synthesis, since the simulated patterns are calculated using only framework atoms, not extra-framework material such as water or template in the cavities. Given the sensitivity of silicoaluminophosphate materials to water at recording temperatures, the molecular sieve samples are calcined after preparation and kept moisture-free according to the following procedure.

About 2 grams of each molecular sieve sample are heated in an oven from room temperature under a flow of nitrogen at a rate of 3° C./minute to 200° C. and, while retaining the nitrogen flow, the sample is held at 200° C. for 30 minutes and the temperature of the oven is then raised at a rate of 2° C./minute to 650° C. The sample is then retained at 650° C. for 8 hours, the first 5 hours being under nitrogen and the final 3 hours being under air. The oven is then cooled to 200° C. at 30° C./minute and, when the XRD pattern is to be recorded, the sample is transferred from the oven directly to a sample holder and covered with Mylar foil to prevent rehydration. Recording under the same conditions immediately after removal of the Mylar foil will also provide a diffraction pattern suitable for use in DIFFaX analysis.

In an alternative embodiment, the intergrown silicoaluminophosphate molecular sieve produced by the method of the invention comprises a plurality of intergrown forms of the CHA and AEI framework types, typically with a first intergrown form having an AEI/CHA ratio of from about 5/95 to about 40/60, as determined by DIFFaX analysis, and a second intergrown form having a different AEI/CHA ratio from said first intergrown form. The second intergrown form typically has an AEI/CHA ratio of about 30/70 to about 55/45, such as about 50/50, as determined by DIFFaX analysis, in which case the XRD diffraction pattern exhibits a broad feature centered at about 16.9 (2θ) in addition to the reflection peaks listed in Table 1.

In yet a further embodiment, the AEI/CHA intergrown molecular sieve produced by the method of the invention comprises at least 50 wt %, such as at least 75 wt %, of an AEI framework type material, as determined by DIFFaX analysis. Such an AEI-rich intergrowth is characterized by a powder XRD diffraction pattern (obtained from a sample after calcination and without rehydration after calcination) having at least the reflections in the 5 to 25 (2θ) range as shown in Table 2 below.

TABLE 2

| 2θ (CuKα) |
|---|
| 9.3-9.6 |
| 12.7-13.0 |
| 13.8-14.0 |
| 15.9-16.1 |
| 16.7-16.9 |
| 18.9-19.1 |
| 20.5-20.7 |
| 23.7-24.0 |

Preferably, the CHA framework type molecular sieve in the AEI/CHA intergrowths described above is SAPO-34 and the AEI framework type molecular sieve is selected from SAPO-18, ALPO-18 and mixtures thereof. In addition, where the intergrown silicoaluminophosphate is a CHA-rich material, the intergrowth preferably has a framework silica to alumina molar ratio ($Si/Al_2$) greater than 0.16 and less than 0.19, such as from about 0.165 to about 0.185, for example about 0.18. The framework silica to alumina molar ratio is conveniently determined by NMR analysis.

Molecular Sieve Synthesis

The AEI and/or CHA framework type silicoaluminophosphate molecular sieves of the invention are synthesized by the hydrothermal crystallization of a source of alumina, a source of phosphorus, a source of silica and at least one organic directing agent. In particular, a reaction mixture comprising sources of silica, alumina and phosphorus, together with water, one or more organic directing agents (R) and optionally seeds from another or the same framework type molecular sieve, is placed in a sealed pressure vessel, optionally lined with an inert plastic such as polytetrafluoroethylene, and heated at a crystallization temperature until a crystalline material is formed. Typically, the reaction mixture has a composition, in terms of mole ratios of oxides, within the following ranges:

| Reactants | Useful | Typical |
|---|---|---|
| $P_2O_5/Al_2O_3$ | 0.6 to 1.2 | 0.75 to 1.1 |
| $SiO_2/Al_2O_3$ | 0 to 0.3 | 0.1 to 0.2 |
| $H_2O/Al_2O_3$ | 25 to 50 | 30 to 45 |
| $R/Al_2O_3$ | 0.5 to 1.2 | 0.7 to 1.0 |

Where the silicoaluminophosphate molecular sieve comprises at least one intergrown phase of a CHA framework type and an AEI framework type, wherein said at least one intergrown phase has an AEI/CHA ratio of from about 5/95 to about 40/60 as determined by DIFFaX analysis, the reaction mixture preferably has a molar composition within the following ranges:

$P_2O_5$: $Al_2O_3$ from about 0.6 to about 1.2,
$SiO_2$: $Al_2O_3$ from about 0.12 to about 0.20,
$H_2O$: $Al_2O_3$ from about 25 to about 50;

and more preferably, within the following ranges:

$P_2O_5$: $Al_2O_3$ from about 0.8 to about 1.1,
$SiO_2$: $Al_2O_3$ from about 0.12 to about 0.15,
$H_2O$: $Al_2O_3$ from about 35 to about 45.

Where the silicoaluminophosphate molecular sieve comprises at least one AEI/CHA intergrown phase comprising at least 50 wt % of the AEI framework type material, as determined by DIFFaX analysis, the reaction mixture preferably has a molar composition within the following ranges:

$P_2O_5$: $Al_2O_3$ from about 0.6 to about 1.2,
$SiO_2$: $Al_2O_3$ from about 0.005 to about 0.15,
$H_2O$: $Al_2O_3$ from about 10 to about 50

Non-limiting examples of suitable silica sources include silicates, fumed silica, for example, Aerosil-200 available from Degussa Inc., New York, N.Y., and CAB-O-SIL M-5, organosilicon compounds such as tetraalkyl orthosilicates, for example, tetramethyl orthosilicate (TMOS) and tetraethylorthosilicate (TEOS), colloidal silicas or aqueous suspensions thereof, for example Ludox HS-40 sol available from E.I. du Pont de Nemours, Wilmington, Del., silicic acid or any combination thereof.

Non-limiting examples of suitable alumina sources include organoaluminum compounds such as aluminum alkoxides, for example aluminum isopropoxide, and inorganic aluminum sources, such as aluminum phosphate, aluminum hydroxide, sodium aluminate, pseudo-boehmite, gibbsite and aluminum trichloride, or any combination thereof. Preferred sources are inorganic aluminum compounds, such as hydrated aluminum oxides and particularly boehmite and pseudoboehmite.

Non-limiting examples of suitable phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A preferred source of phosphorus is phosphoric acid.

The organic directing agent employed in the synthesis method of the invention will depend on the particular silicoaluminophosphate molecular sieve being targeted. Suitable organic directing agents for the production of CHA framework-type silicoaluminophosphate molecular sieves include tetraethylammonium hydroxide, tetraethylammonium fluoride, isopropylamine, dipropylamine, cyclohexylamine, triethylamine, triethanolamine, N-methylethanolamine, N-methyldiethanolamine, N,N-dimethylethanolamine, N,N,-diethylethanolamine, dimethylpropanolamine, 1-(N,N-demethylamino)-2-propanol, morpholine and mixtures thereof. Suitable organic directing agents for the production of AEI framework-type silicoaluminophosphate molecular sieves include tetraethylammoniumhydroxide, tertraethylamrnmoniumbromide, tertraethylammoniumcloride, N,N-diisopropylethylamine, and mixtures thereof. Suitable organic directing agents for the production of intergrown AEI/CHA framework-type silicoaluminophosphate molecular sieves include tetraethyl ammonium compounds and, in particular tetraethyl ammonium hydroxide.

Most commercial sources of the silica, alumina, and phosphorus and organic directing agent listed above contain significant levels of impurities, including alkali metals. For example, certain commercial sources of TEAOH contain as much as 1.6 wt % potassium and 0.05 wt % of sodium, whereas phosphoric acid, a preferred phosphorus source, frequently contains in excess of 0.01 wt % of alkali metal. According to the present invention, it has now been found that the level of alkali metal, particularly sodium and potassium, impurities in the synthesis mixture has an important role in determining the average crystal size and the crystal size distribution of CHA and AEI-containing materials. In particular, it is found that the synthesis of CHA and AEI-containing materials having an average ($d_{50}$) crystal size of less than 2.2 micron and a relatively low crystal size distribution ($d_{90}-d_{10}$)/$d_{50}$ of less than 1.0 is facilitated when the synthesis mixtures contains between about 0.08 and about 0.90, such as between about 0.08 and about 0.80 ppm wt, for example between about 0.10 and about 0.50 g of alkali metal/mole of alumina.

Moreover, in the synthesis of AEI/CHA intergrowths, it is found that the CHA character of the intergrowth is reduced in favor of the AEI component when the alkali metal content is at least 1.00 g/mole of alumina, such as from 1.00 to 2.50 g/mole of alumina.

After combining all the components of the reaction mixture, the mixture is desirably allowed to age at a temperature of between about 10° C. and about 30° C. for a time up to about 12 hours. Conveniently, the reaction mixture is agitated during the aging step.

After the optional aging step, the reaction mixture is sealed in a vessel and heated, preferably under autogenous pressure, to a temperature in the range of from 100° C. to about 350° C., for example from about 125° C. to about 250° C., such as from about 150° C. to about 200° C. The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out without or, more preferably, with agitation.

Once the crystalline molecular sieve product is formed, usually in a slurry state, it may be recovered by any standard technique well known in the art, for example, by centrifugation or filtration. The recovered crystalline product may then be washed, such as with water, and then dried, such as in air.

In one practical embodiment, the synthesis is conducted as a continuous process in a tubular reactor. In such a process, two reagent streams could be introduced into the tubular reactor, one stream comprising the alumina source dispersed in a low reactive medium, such as a neutral solution containing part of the phosphoric acid and the organic directing agent, and the other stream comprising the remaining reagents in an acidic "reactive" medium. After an optional pretreatment, for example where the synthesis proceeds through formation of a precursor, the streams could be combined by an in-line mixer and pumped through the tubular reactor at an elevated temperature, such as the crystallization temperature. Different zones of reactor could be used for the pretreatment and the crystallization and, by controlling the flow rate and length of the zones, the desired residence time in each zone could be achieved.

As a result of the synthesis process, the crystalline product recovered from the reaction mixture contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system.

Molecular Sieve Catalyst Compositions

The silicoaluminophosphate molecular sieves produced by the synthesis method of the invention are particularly intended for use as organic conversion catalysts. Before use in catalysis, the molecular sieves will normally be formulated into catalyst compositions by combination with other materials, such as binders and/or matrix materials, which provide additional hardness or catalytic activity to the finished catalyst.

Materials which can be blended with the molecular sieve can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of molecular sieve contained in the final catalyst product ranges from 10 to 90 weight percent of the total catalyst, preferably 20 to 80 weight percent of the total catalyst composition.

Use of the Molecular Sieve

The silicoaluminophosphate molecular sieves produced by the method of the invention are useful as catalysts in a variety of processes including cracking of, for example, a naphtha feed to light olefin(s) or higher molecular weight (MW) hydrocarbons to lower MW hydrocarbons; hydrocracking of, for example, heavy petroleum and/or cyclic feedstock; isomerization of, for example, aromatics such as xylene; polymerization of, for example, one or more olefin(s) to produce a polymer product; reforming; hydrogenation; dehydrogenation; dewaxing of, for example, hydrocarbons to remove straight chain paraffins; absorption of, for example, alkyl aromatic compounds for separating out isomers thereof; alkylation of, for example, aromatic hydrocarbons such as benzene and alkyl benzene, optionally with propylene to produce cumene or with long chain olefins; transalkylation of, for example, a combination of aromatic and polyalkylaromatic hydrocarbons; dealkylation; dehydrocyclization; disproportionation of, for example, toluene to make benzene and par-axylene; oligomerization of, for example, straight and branched chain olefin(s); and the synthesis of monoalkylamines and dialkylamines.

The silicoaluminophosphate molecular sieves produced by the method of the invention are particularly suitable as catalysts for use in the conversion of oxygenates to olefins. As used herein, the term "oxygenates" is defined to include, but is not necessarily limited to aliphatic alcohols, ethers, carbonyl compounds (aldehydes, ketones, carboxylic acids, carbonates, and the like), and also compounds containing heteroatoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$-$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 hr$^{-1}$ to about 500 hr$^{-1}$, such as in the range of from about 0.5 hr$^{-1}$ to about 300 hr$^{-1}$, for example in the range of from about 0.1 hr$^{-1}$ to about 200 hr$^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

Using the various oxygenate feedstocks discussed above, particularly a feedstock containing methanol, a catalyst composition of the invention is effective to convert the feedstock primarily into one or more olefin(s). The olefin(s) produced typically have from 2 to 30 carbon atoms, preferably 2 to 8 carbon atoms, more preferably 2 to 6 carbon atoms, still more preferably 2 to 4 carbons atoms, and most preferably are ethylene and/or propylene. The resultant olefins can be separated from the oxygenate conversion product for sale or can be fed to a downstream process for converting the olefins to, for example, polymers.

The invention will now be more particularly described with reference to the following Examples.

In the Examples, DIFFaX analysis was used to determine the AEI/CHA ratio of the molecular sieves. Simulated powder XRD diffraction patterns for varying ratios of AEI/CHA were generated using the DIFFaX program available from the International Zeolite Association (see also M. M. J. Tracey et al., Proceedings of the Royal Chemical Society, London, A (1991), Vol. 433, pp. 499-520 "Collection of Simulated XRD Powder Patterns for Zeolites" by M. M. J. Treacy and J. B. Higgins, 2001, Fourth Edition, published on behalf of the Structure Commission of the International Zeolite Association). The DIFFaX input file used to simulate the XRD diffraction patterns is given in Table 2 of U.S. Patent Application Publication No. 2002/0165089, incorporated herein by reference. In order to obtain best fitting between the DIFFaX simulated patterns and the experimental patterns, two sets of simulated XRD patterns were generated using a line broadening of 0.009 (as described in U.S. Patent Application No. 2002/0165089) and a line broadening of 0.04 (FIGS. 1a and 1b). The simulated diffraction patterns were then compared with the experimental powder XRD diffraction patterns. In this respect, a very sensitive range is the 15 to 19.5 2θ range.

Crystal size measurements in the Examples were taken with a Malvern Mastersizer 2000 (d values being expressed by volume).

EXAMPLE 1 (COMPARATIVE)

A mixture of 385.65 g of phosphoric acid (85% in water, Acros, containing 122 ppm Na and 4 ppm K), 369.53 g of demineralized water and 701.49 g of tetraethylammonium hydroxide solution (35% in water, Sachem, containing 2 ppm Na and 26 ppm K) was prepared in a 2 liter polyethylene bottle. The resultant mixture was then transferred to a glass beaker placed in a Neslab bath at 30° C. and, after initiating stirring of the mixture with a laboratory mixer, 37.27 g Ludox AS 40 (40% silica, containing 815 ppm of Na and 39 ppm of K) was added to the beaker followed by 227.01 g of alumina (Condea Pural SB-1, containing 18 ppm of Na and 26 ppm of K). A slurry was produced and was then aged for 2 hours in the Neslab bath at 30° C. with the stirring being continued. The composition of the mixture in terms of molar ratios was as follows:

$$0.15SiO_2/Al_2O_3/P_2O_5/TEAOH/35H_2O$$

The Na and K content of the overall synthesis mixture, resulting from the presence of these elements in the raw materials, was 0.035 g/mole of alumina and 0.007 g/mole of alumina respectively. The mixture was transferred to a 2 liter PARR stainless steel autoclave and heated 20° C./hour to 165° C. The mixture was stirred with a laboratory mixer at 200 rpm (tip speed of 1.3 m/s) during the whole hydrothermal treatment. The autoclave was kept at 165° C. for 60 hours.

After cooling to room temperature, the slurry was washed and dried and an X-ray diffraction pattern of the crystalline product was taken after the calcination procedure described above. Using this diffraction pattern, DIFFaX analysis was conducted and showed the crystalline product to contain an AEI/CHA intergrowth comprising 28 wt % of an AEI framework type molecular sieve and 72 wt % of a CHA framework type molecular sieve. The framework silica to alumina molar ratio (Si/Al$_2$) of the crystalline product was found to be 0.19. In addition, the product had a d$_{50}$ particle size of 2.0 μm and a span [(d$_{90}$–d$_{10}$)/d$_{50}$] of 0.8.

EXAMPLES 2 TO 4 (COMPARATIVE)

Several samples were prepared as in Example 1 and the results are summarized in the following table.

| Example | D50 (micron) | Span | DIFFaX AEI/CHA ratio |
|---|---|---|---|
| 1 | 2.0 | 0.8 | 28/72 |
| 2 | 1.7 | 0.8 | n/a |
| 3 | 1.5 | 0.8 | n/a |
| 4 | 1.5 | 0.8 | 29/71 |

EXAMPLES 5 TO 12

Several mixtures were prepared in the same manner as in Example 1, but with variable amounts of Na and/or K added in the form of their chloride salts. The results are summarized in the following table.

| Example | g Na/mole alumina | g K/mole alumina | D50 (micron) | Span | DIFFaX AEI/CHA ratio |
|---|---|---|---|---|---|
| 5 | 0.087 | 0.007 | 1.6 | 0.8 | 28/72 |
| 6 | 0.340 | 0.007 | 1.8 | 0.7 | 28/72 |
| 7 | 0.550 | 0.007 | 1.6 | 0.8 | 25/75 |
| 8 | 0.035 | 0.059 | 1.6 | 0.8 | 29/71 |
| 9 | 0.035 | 0.213 | 1.6 | 0.7 | 28/72 |
| 10 | 0.035 | 0.522 | 1.6 | 0.8 | 28/72 |
| 11 | 1.064 | 0.007 | 0.6 | 4.1 | 75/25 |
| 12 | 2.094 | 0.007 | 3.3 | 2.2 | 85/15 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for making an olefin product from an oxygenate feedstock comprising:
   (1) contacting an oxygenate feedstock comprising methanol, dimethyl ether, or a mixture thereof with a silicoaluminophosphate molecular sieve catalyst comprising a CHA framework type material, an AEI framework type material, or a material comprising at least one intergrown phase of an AEI framework type and a CHA framework type, and made by a method comprising:
      (a) preparing a synthesis mixture comprising water, an organic directing agent, and sources of phosphorus, alumina and silica, wherein the total amount of alkali metal present in said synthesis mixture is from about 0.08 to about 0.90 g/mole alumina;
      (b) heating said synthesis mixture to a crystallization temperature of between about 100° C. and about 300° C.; and
      (c) recovering said molecular sieve, wherein the contacting of the feedstock and the catalyst forms an olefin product comprising ethylene and propylene; and
   (2) converting at least part of the olefin product to polymer.
2. The process of claim 1, wherein the total amount of alkali metal present in said synthesis mixture is from about 0.08 to about 0.80 g/mole alumina.
3. The process of claim 1, wherein the total amount of alkali metal present in said synthesis mixture is from about 0.10 to about 0.50 g/mole alumina.
4. The process of claim 1, wherein said silicoaluminophosphate molecular sieve comprises a CHA framework type material.
5. The process of claim 1, wherein said silicoaluminophosphate molecular sieve comprises an AEI framework type material.
6. The process of claim 1, wherein said silicoaluminophosphate molecular sieve is a material comprising at least one intergrown phase of an AEI framework type and a CHA framework type.
7. The process of claim 6, wherein said at least one intergrown phase has an AEI/CHA ratio of from about 5/95 to about 40/60, as determined by DIFFaX analysis.
8. The process of claim 6, wherein said at least one intergrown phase has an AEI/CHA ratio of from about 10/90 to about 30/70, as determined by DIFFaX analysis.
9. The process of claim 6, wherein said at least one intergrown phase has an AEI/CHA ratio of from about 15/95 to about 20/80, as determined by DIFFaX analysis.
10. The process of claim 7, wherein said silicoaluminophosphate molecular sieve has an X-ray diffraction pattern comprising at least one reflection peak in each of the following ranges in the 5 to 25 (2θ) range:

| 2θ (CuKα) |
|---|
| 9.3-9.6 |
| 12.7-13.0 |
| 13.8-14.0 |
| 15.9-16.1 |
| 17.7-18.1 |
| 18.9-19.1 |
| 20.5-20.7 |
| 23.7-24.0. |

11. The process of claim 6, wherein said silicoaluminophosphate molecular sieve comprises first and second intergrown forms each of an AEI framework type material and a CHA framework type material.

12. The process of claim 11, wherein said first intergrown form has an AEI/CHA ratio of from about 5/95 to about 40/60 as determined by DIFFaX analysis and said second intergrown form has a different AEI/CHA ratio from said first intergrown form.

13. The process of claim 12, wherein said second intergrown form has an AEI/CHA ratio of about 30/70 to about 55/45, as determined by DIFFaX analysis.

14. The process of claim 12, wherein said second intergrown form has an AEI/CHA ratio of about 50/50, as determined by DIFFaX analysis.

15. The process of claim 1, wherein the heating (b) is conducted in a continuous synthesis apparatus having an inlet, through which said synthesis mixture is introduced, and an outlet, through which said molecular sieve is recovered.

16. The process of claim 1, wherein the heating in (b) is done under agitation and the silicoaluminophosphate molecular sieve comprises at least one intergrown phase of a CHA framework type and an ALT framework type, wherein said at least one intergrown phase has an ARL/CHA ratio of from about 5/95 to about 40/60 as determined by DIFFaX analysis, and wherein said synthesis mixture has a molar composition within the following ranges:

$P_2O_5$: $Al_2O_3$ from about 0.6 to about 1.2,
$SiO_2$: $Al_2O_3$ from about 0.12 to about 0.20,
$H_2O$: $Al_2O_3$ from about 25 to about 50.

17. The process of claim 16, wherein the alkali metal present in said synthesis mixture is sodium and/or potassium.

18. The process of claim 16, wherein said synthesis mixture has a molar composition within the following ranges:

$P_2O_5$: $Al_2O_3$ from about 0.8 to about 1.1,
$SiO_2$: $AL_2O_3$ from about 0.12 to about 0.15,
$H_2O$: $Al_2O_3$ from about 35 to about 45.

19. The process of claim 16, wherein said organic directing agent comprises a tetraethylammonium compound.

20. The process of claim 16, wherein the heating in (b) is conducted so as to raise the temperature of said mixture at a rate of at least 8° C./hour.

21. The process of claim 16, wherein the heating in (b) is conducted so as to raise the temperature of said mixture at a rate of from about 10° C./hour to about 40° C./hour.

22. The process of claim 16, wherein said agitation is conducted so as to prevent precipitation of the synthesis mixture components.

23. The process of claim 16, wherein said crystallization temperature is between about 150° C. and about 200° C.

24. The process of claim 1, wherein the silicoaluminophosphate molecular sieve has an average ($d_{50}$) crystal size of less than 2.2 micron.

25. The process of claim 1, wherein the silicoaluminophosphate molecular sieve has an average ($d_{50}$) crystal size of between about 1.5 micron and about 1.9 micron.

26. The process of claim 1, wherein the silicoaluminophosphate molecular sieve has a ($d_{90}$–$d_{10}$)/$d_{50}$ crystal size distribution less than 1.0.

* * * * *